United States Patent
Yasuda et al.

(10) Patent No.: US 7,544,841 B2
(45) Date of Patent: Jun. 9, 2009

(54) PRODUCTION METHOD OF PHENYLETHANOLAMINE COMPOUND, AND ITS INTERMEDIATE

(75) Inventors: Nobuyuki Yasuda, Tokyo (JP); Tsuyoshi Kajita, Kawasaki (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 11/577,652

(22) PCT Filed: Oct. 19, 2005

(86) PCT No.: PCT/JP2005/019176

§ 371 (c)(1), (2), (4) Date: Apr. 20, 2007

(87) PCT Pub. No.: WO2006/043577

PCT Pub. Date: Apr. 27, 2006

(65) Prior Publication Data

US 2007/0287864 A1    Dec. 13, 2007

(30) Foreign Application Priority Data

Oct. 20, 2004 (JP) ................. 2004-305296

(51) Int. Cl.
*C07C 211/00* (2006.01)
(52) U.S. Cl. .................................. 564/307
(58) Field of Classification Search ........... 564/360
See application file for complete search history.

(56) References Cited

U.S. PATENT DOCUMENTS

| | | | | |
|---|---|---|---|---|
| 2,538,792 A | * | 1/1951 | Moerch | 564/357 |
| 5,149,874 A | * | 9/1992 | Jacobson | 564/248 |
| 6,069,176 A | * | 5/2000 | Tsuchiya et al. | 514/646 |
| 6,586,634 B1 | | 7/2003 | Hof | |
| 2002/0143211 A1 | * | 10/2002 | Dolitzky et al. | 564/316 |

FOREIGN PATENT DOCUMENTS

| | | |
|---|---|---|
| EP | 0 890 571 A1 | 1/1999 |
| EP | 0 940 387 A1 | 9/1999 |
| WO | WO 97/15549 A1 | 5/1997 |

OTHER PUBLICATIONS

Howe et al., *Journal of Medicinal Chemistry*, 35 (10): 1751-1759 (1992).

* cited by examiner

*Primary Examiner*—Paul A Zucker
(74) *Attorney, Agent, or Firm*—Leydig, Voit & Mayer, Ltd.

(57) ABSTRACT

A novel production method for a phenylethanolamine compound of the following general formula (III):

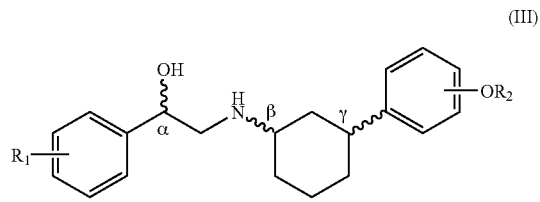

(wherein $R_1$ represents a hydrogen atom or a halogen atom; $R_2$ represents an alkyl group optionally substituted with an alkoxycarbonyl group); and a novel production intermediate for it.

27 Claims, No Drawings

PRODUCTION METHOD OF PHENYLETHANOLAMINE COMPOUND, AND ITS INTERMEDIATE

DETAILED DESCRIPTION OF THE INVENTION

1. Technical Field

The present invention relates to a novel method for producing ethyl 3-[(1R,3R)-3-[(2R)-2-(3-chlorophenyl)-2-hydroxyethylamino]cyclohexyl]phenoxyacetate and its pharmaceutically-acceptable salt, and to its intermediate.

2. Background Art

Patent Reference 1 discloses a phenylethanolamine compound having a selective $\beta_3$-adrenaline receptor-stimulating effect and a method for producing it.

The outline of the production method described in Patent Reference 1 is as follows:

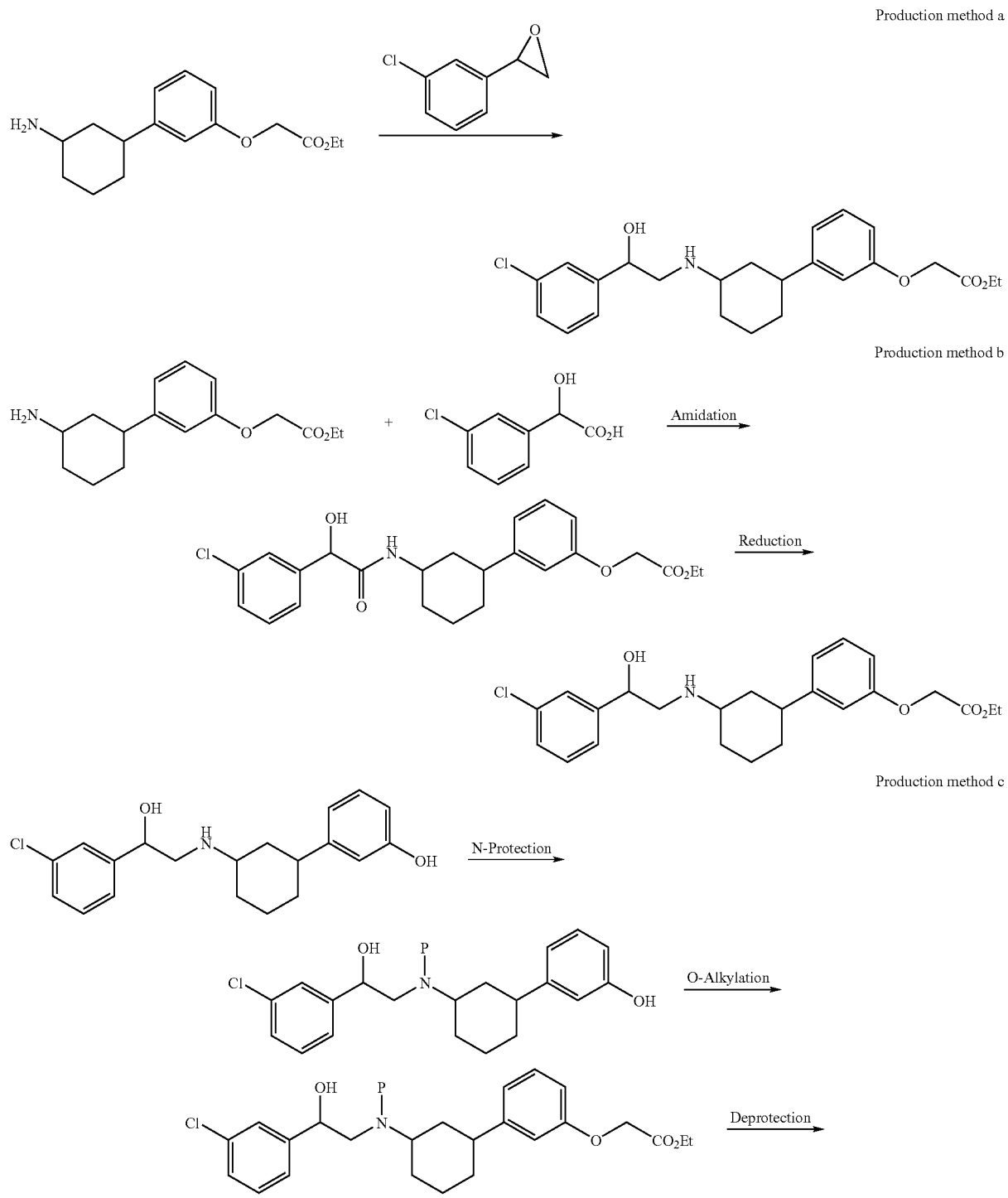

Production method a

Production method b

Production method c

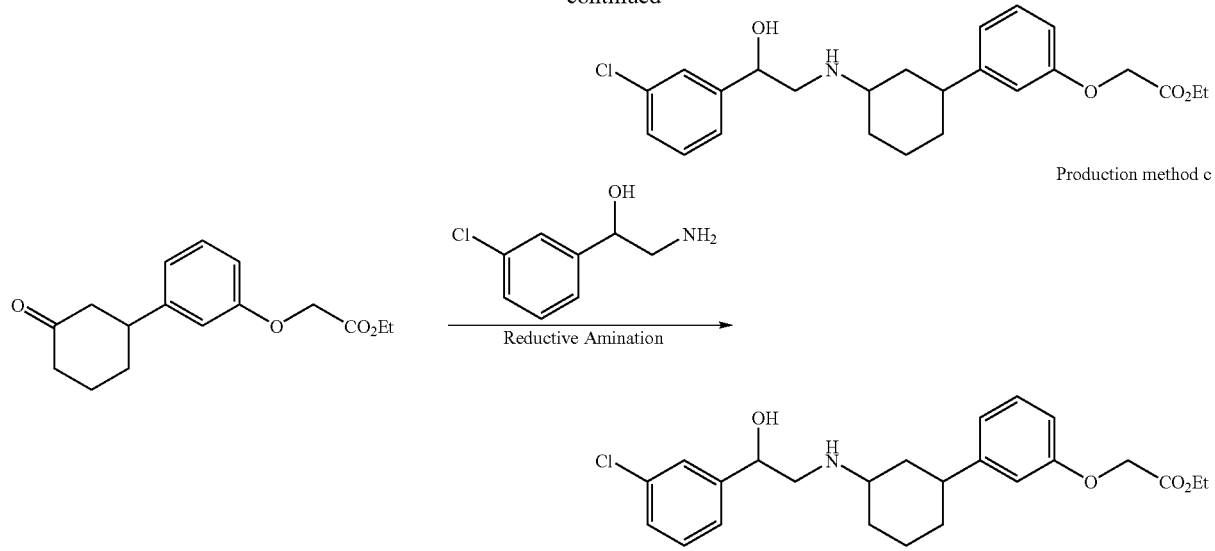

Production method c

Both the production methods a and b go on by way of the following intermediate:

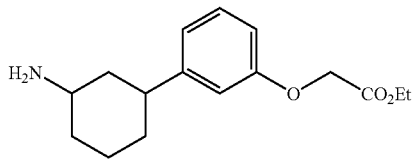

For efficiently producing the intermediate, the methods take a process of protecting the amino group of 3-(3-hydroxyphenyl)cyclohexylamine, then alkylating (this includes alkoxycarbonylalkylation) the phenolic hydroxyl group, and further deprotecting the protective group of the amino group.

The production method c also includes a process of deprotecting the amino group with a protective group, and this is unfavorable from the viewpoint of the material expenses and the number of the steps.

The production method d is problematic in point of the stereoselectivity in the reductive amination reaction and the resolution.

In general, in case of a compound having plural reactive points such as an amino group, an alcoholic hydroxyl group and a phenolic hydroxyl group, it is well known that, when the phenolic hydroxyl group is selectively alkylated (this includes alkoxycarbonylalkylation), then an alkylated amino group-having side product is produced since the reactivity of the amino group is higher than that of the phenolic hydroxyl group. Specifically, in many ethanolamine skeleton-having compounds, since the nucleation at the amino group may more readily go on, it is general that the amino group is first protected so as to inactivate the nucleophilic nitrogen atom thereof, and thereafter the phenolic hydroxyl group is reacted.

As opposed to this, also reported is a case of direct and selective alkoxycarbonylalkylation of the phenolic hydroxyl group of an ethanolamine skeleton-having compound without using a protective group (Non-Patent Reference 1).

In these reactions, however, a reactant such as sodium hydride or N,N-dimethylformamide is used, and therefore the system becomes an alkaline aqueous solution since water is used in the workup step, and accordingly, there may be a problem in that the ester bond of the product may be hydrolyzed and the product may be converted into a carboxylic acid whereby the yield of the intended compound may lower.

A carbonyl group-having solvent is advantageous in that the solubility of an inorganic substance therein is low and therefore its removal is easy, and accordingly, the solvent is favorable for the intended alkoxycarbonylalkylation on an industrial scale. However, the carbonyl group-having solvent has a drawback in that the reaction speed in it is low and N-alkylation may often takes first priority therein.

The production of side products and the removal of reactants as mentioned above are significant problems in production of medicines, and at present, a production method where the side product is as small as possible especially in the final production step is desired.

Accordingly, for a compound having an amino group, an alcoholic hydroxyl group and a phenolic hydroxyl group and represented by the following general formula (I):

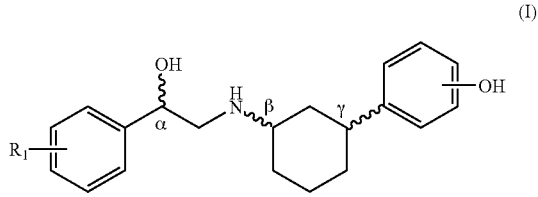

(wherein $R_1$ represents a hydrogen atom or a halogen atom), a reaction is desired that enables direct and highly-selective alkylation (this includes alkoxycarbonylalkylation) of the phenolic hydroxyl group in the compound. Further, for alkoxycarbonylalkylation, a reaction is desired that may give a desired product without using water so as not to promote hydrolysis of the ester in the workup step.

In particular, in production of ethyl 3-[(1R,3R)-3-[(2R)-2-(3-chlorophenyl)-2-hydroxyethylamino]cyclohexyl]phenoxyacetate, the process has a problem in that many intermediates in the constitutive steps are oily and much labor is needed for purifying them in the industrial-scale process.

In production of medicines, the quality management of intermediates near the final stage of the process shall be severer, and therefore compounds having a constant quality must be obtained all the time by defining in detail the process condition such as the equivalent number of the substrate and the reaction temperature.

In this respect, when the intermediate could be obtained as a crystal, then it may be isolated and purified through easy operation such as crystallization or recrystallization, and therefore this is excellent in point of its quality management, and is advantageous in that it enables accurate measurement in the next step.

Accordingly, for the present reaction, desired are a crystallizable intermediate with good crystallinity and a production method that goes on by way of the intermediate.

Patent Reference 1: WO97/15549

Non-Patent Reference 1: Journal of Medicinal Chemistry (Vol. 35, p. 1751)

DISCLOSURE OF THE INVENTION

Problems that the Invention is to Solve

An object of the invention is to provide a novel production method for a phenylethanolamine compound useful as medicines and represented by the following general formula (III):

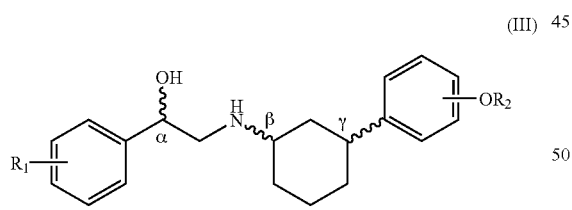

(wherein $R_1$ represents a hydrogen atom or a halogen atom; $R_2$ represents an alkyl group optionally substituted with an alkoxycarbonyl group), and a novel production intermediate for it.

Means for Solving the Problems

We, the present inventors have assiduously studied for the purpose of solving the above-mentioned problems, and have found out an industrially-favorable production method for a phenylethanolamine compound and a novel production intermediate for it, and have completed the present invention.

Specifically, the subject matter of the invention includes the following:

(1) A solvate of 1-(3-chlorophenyl)-2-[3-(3-hydroxyphenyl)cyclohexylamino]ethanol represented by the following formula:

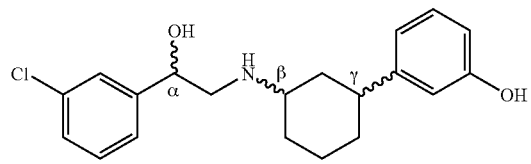

(2) The solvate as described in (1), wherein the absolute configuration of the asymmetric carbon α is R-configuration.

(3) The solvate as described in (1) or (2), wherein the absolute configuration of the asymmetric carbon β is R-configuration.

(4) The solvate as described in any of (1) to (3), wherein the absolute configuration of the asymmetric carbon γ is R-configuration.

(5) The solvate as described in any of (1) to (4), which is (1R)-1-(3-chlorophenyl)-2-[(1R,3R)-3-(3-hydroxyphenyl)cyclohexylamino]ethanol 1/3 toluene-solvate.

(6) The solvate as described in any of (1) to (4), which is (1R)-1-(3-chlorophenyl)-2-[(1R,3R)-3-(3-hydroxyphenyl)cyclohexylamino]ethanol 1/3 ethyl acetate-solvate.

(7) The solvate as described in any of (1) to (6), which is a crystal.

(8) The solvate as described in any of (1) to (5) or (7), which is a crystal of (1R)-1-(3-chlorophenyl)-2-[(1R,3R)-3-(3-hydroxyphenyl)cyclohexylamino]ethanol 1/3 toluene-solvate.

(9) The solvate as described in any of (1) to (4), (6) or (7)), which is a crystal of (1R)-1-(3-chlorophenyl)-2-[(1R,3R)-3-(3-hydroxyphenyl)cyclohexylamino]ethanol 1/3 ethyl acetate-solvate.

(10) A production method of a crystal of (1R)-1-(3-chlorophenyl)-2-[(1R,3R)-3-(3-hydroxyphenyl)cyclohexylamino]ethanol 1/3 toluene-solvate, which comprises reacting a compound represented by the following formula:

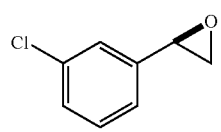

with (1R,3R)-3-(3-hydroxyphenyl)cyclohexylamine in toluene.

(11) A production method of a crystal of (1R)-1-(3-chlorophenyl)-2-[(1R,3R)-3-(3-hydroxyphenyl)cyclohexylamino]ethanol 1/3 ethyl acetate-solvate, which is obtained through treatment of a compound represented by the following formula:

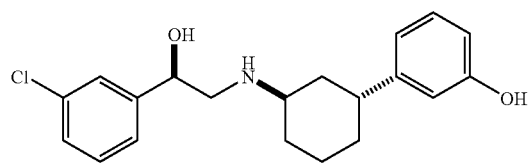

(1/3 toluene-solvate), with ethyl acetate.

(12) A production method of a compound represented by the following general formula (III) or its pharmaceutically-acceptable salt, or their hydrate or solvate:

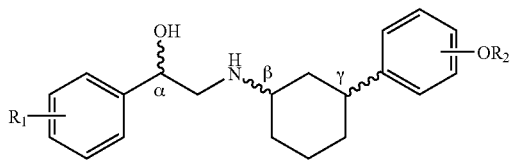

(III)

(wherein $R_1$ represents a hydrogen atom or a halogen atom; $R_2$ represents an alkyl group optionally substituted with an alkoxycarbonyl group), which comprises reacting, without protecting the amino group thereof, a compound represented by the following general formula (I):

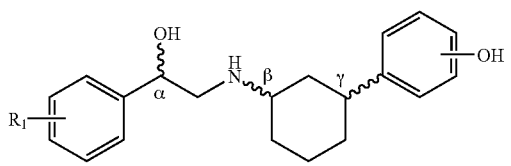

(I)

(wherein $R_1$ represents a hydrogen atom or a halogen atom), with a compound represented by the following general formula (II):

$R_2$—X     (II)

(wherein $R_2$ represents an alkyl group optionally substituted with an alkoxycarbonyl group; X represents a halogen atom).

(13) The production method as described in (12), wherein the compound of formula (I) is obtained by reacting a compound represented by the following general formula (IV):

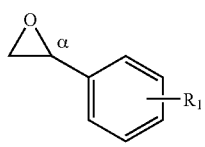

(IV)

(wherein $R_1$ represents a hydrogen atom or a halogen atom), with a compound represented by the following formula (V):

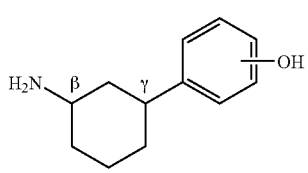

(V)

(14) The production method as described in (12) or (13), wherein the compound represented by formula (I) or its solvate is reacted with the compound represented by formula (II) in the presence of a carbonate.

(15) The production method as described in any of (12) to (14), wherein the compound represented by formula (I) or its solvate is reacted with the compound represented by formula (II) in the presence of potassium carbonate.

(16) The production method as described in any of (12) to (15), wherein the compound represented by formula (I) or its solvate is reacted with the compound represented by formula (II) in the presence of finely-ground potassium carbonate.

(17) The production method as described in any of (12) to (16), wherein the compound represented by formula (I) or its solvate is reacted with the compound represented by formula (II) in a carbonyl group-having solvent.

(18) The production method as described in any of (12) to (17), wherein the compound represented by formula (I) is reacted with the compound represented by formula (II) in methyl ethyl ketone.

(19) The production method as described in any of (12) to (18), wherein $R_1$ is a halogen atom.

(20) The production method as described in any of (12) to (19), wherein $R_1$ is a chlorine atom.

(21) The production method as described in any of (12) to (20), wherein $R_2$ is a methyl group substituted with one alkoxycarbonyl group having from 2 to 5 carbon atoms.

(22) The production method as described in any of (12) to (21), wherein $R_2$ is an ethoxycarbonylmethyl group.

(23) The production method as described in any of (12) to (22), wherein the absolute configuration of the asymmetric carbon α is R-configuration.

(24) The production method as described in any of (12) to (23), wherein the absolute configuration of the asymmetric carbon β is R-configuration.

(25) The production method as described in any of (12) to (24), wherein the absolute configuration of the asymmetric carbon γ is R-configuration.

(26) The production method as described in any of (12) to (25), wherein the compound represented by formula (I) or its solvate is a solvate of (1R)-1-(3-chlorophenyl)-2-[(1R,3R)-3-(3-hydroxyphenyl)cyclohexylamino]ethanol.

(27) The production method as described in any of (12) to (26), wherein the compound represented by formula (I) or its solvate is (1R)-1-(3-chlorophenyl)-2-[(1R,3R)-3-(3-hydroxyphenyl)cyclohexylamino]ethanol 1/3 toluene-solvate.

(28) The production method as described in any of (12) to (26), wherein the compound represented by formula (I) or its solvate is (1R)-1-(3-chlorophenyl)-2-[(1R,3R)-3-(3-hydroxyphenyl)cyclohexylamino]ethanol 1/3 ethyl acetate-solvate.

(29) The production method as described in any of (12) to (28), wherein the compound represented by formula (I) or its solvate is a crystal of a solvate of (1R)-1-(3-chlorophenyl)-2-[(1R,3R)-3-(3-hydroxyphenyl)cyclohexylamino]ethanol.

(30) The production method as described in any of (12) to (27) or (29), wherein the compound represented by formula (I) or its solvate is a crystal of (1R)-1-(3-chlorophenyl)-2-[(1R,3R)-3-(3-hydroxyphenyl)cyclohexylamino]ethanol 1/3 toluene-solvate.

(31) The production method as described in any of (12) to (26), (28) or (29), wherein the compound represented by formula (I) or its solvate is a crystal of (1R)-1-(3-chlorophenyl)-2-[(1R,3R)-3-(3-hydroxyphenyl)cyclohexylamino] ethanol 1/3 ethyl acetate-solvate.

(32) The production method as described in any of (12) to (31), wherein the pharmaceutically-acceptable salt of the compound represented by formula (III) is a maleate.

(33) The production method as described in any of (12) to (27), (29), (30) or (32), which comprises reacting a crystal of (1R)-1-(3-chlorophenyl)-2-[(1R,3R)-3-(3-hydroxyphenyl) cyclohexylamino]ethanol 1/3 toluene-solvate as a starting material, with ethyl bromoacetate in methyl ethyl ketone in the presence of potassium carbonate, and adding maleic acid thereto.

(34) The production method as described in any of (12) to (27), (29), (30), (32) or (33), which comprises reacting a crystal of (1R)-1-(3-chlorophenyl)-2-[(1R,3R)-3-(3-hydroxyphenyl)cyclohexylamino]ethanol 1/3 toluene-solvate as a starting material, with ethyl bromoacetate in methyl ethyl ketone in the presence of finely-ground potassium carbonate, and adding maleic acid thereto.

(35) The production method as described in any of (12) to (26), (28), (29), (31) or (32), which comprises reacting a crystal of (1R)-1-(3-chlorophenyl)-2-[(1R,3R)-3-(3-hydroxyphenyl)cyclohexylamino]ethanol 1/3 ethyl acetate-solvate as a starting material, with ethyl bromoacetate in methyl ethyl ketone in the presence of potassium carbonate, and adding maleic acid thereto.

(36) The production method as described in any of (12) to (26), (28), (29), (31), (32) or (35), which comprises reacting a crystal of (1R)-1-(3-chlorophenyl)-2-[(1R,3R)-3-(3-hydroxyphenyl)cyclohexylamino]ethanol 1/3 ethyl acetate-solvate as a starting material, with ethyl bromoacetate in methyl ethyl ketone in the presence of fine-ground potassium carbonate, and adding maleic acid thereto.

(37) The production method as described in any of (12) to (36), wherein in HPLC analysis of the reaction solution after the reaction, the relative area percentage of the peak derived from the compound represented by formula (I) or its solvate, (1R)-1-(3-chlorophenyl)-2-[(1R,3R)-3-(3-hydroxyphenyl) cyclohexylamino]ethanol 1/3 toluene-solvate, or (1R)-1-(3-chlorophenyl)-2-[(1R,3R)-3-(3-hydroxyphenyl)cyclohexylamino]ethanol 1/3-ethyl acetate solvate is at most about 1.0%.

(38) The production method as described in any of (14) to (37), wherein the carbonate or potassium carbonate is ground with a jet mill.

(39) The production method as described in any of (14) to (38), wherein the carbonate or potassium carbonate has a mean particle size of at most about 10 micrometers.

Effect of the Invention

According to the invention, a compound of the following formula (III):

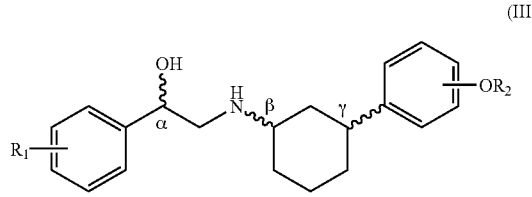

(III)

(wherein $R_1$ represents a hydrogen atom or a halogen atom; $R_2$ represents an alkyl group optionally substituted with an alkoxycarbonyl group)

can be produced efficiently. This is because the invention has enabled direct and highly-selective alkylation (this includes alkoxycarbonylalkylation) of a compound of the following general formula (I):

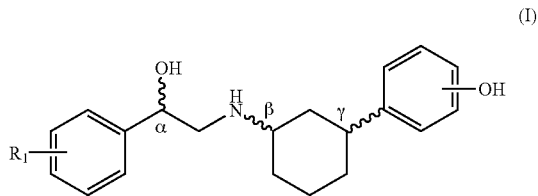

(I)

(wherein $R_1$ represents a hydrogen atom or a halogen atom) at the phenolic hydroxyl group thereof; and the invention has made it possible to obtain an intermediate which is easy to isolate and purify and which has good crystallinity.

BEST MODE FOR CARRYING OUT THE INVENTION

The invention is described in detail hereinunder. In the general formulae in the invention, $R_1$ is a hydrogen atom or a halogen atom. A preferred example of $R_1$ is a halogen atom. Examples of the halogen atom include fluorine, chlorine, bromine and iodine; and a preferred example thereof is a chlorine atom.

$R_2$ is an alkyl group optionally substituted with an alkoxycarbonyl group, and its examples include an alkyl group having from 1 to 4 carbon atoms, and an alkyl group having from 1 to 4 carbon atoms and substituted with one or two alkoxycarbonyl groups having from 2 to 5 carbon atoms. A preferred example of $R_2$ is an alkyl group having from 1 to 4 carbon atoms and substituted with one alkoxycarbonyl group having from 2 to 5 carbon atoms; and a more preferred example thereof is an ethoxycarbonylmethyl group. Examples of the alkyl group having from 1 to 4 carbon atoms include a methyl group, an ethyl group, a normal propyl group, an iso-propyl group, a normal butyl group, an isobutyl group, an s-butyl group, a t-butyl group; and a preferred example thereof is a methyl group. Examples of the alkoxycarbonyl group having from 2 to 5 carbon atoms, which is a substituent of the alkyl group having from 1 to 4 carbon atoms, include a methoxycarbonyl group, an ethoxycarbonyl group, a normal propoxycarbonyl group, an isopropoxycarbonyl group, a normal butoxycarbonyl group, an isobutoxycarbonyl group, an s-butoxycarbonyl group, a t-butoxycarbonyl group; and a preferred example thereof is an ethoxycarbonyl group. The number of the substituents is 1 or 2, preferably 1.

X is a halogen atom. A preferred example of X is bromine.

The absolute configuration of the asymmetric carbons α, β and γ may be R or S, but all are preferably in R-configuration.

The compound of formula (III) may be obtained by reacting compounds of formulae (I) and (II), and when a carbonate is added thereto, the compound of formula (III) may be obtained at a high yield. In other words, this means that the starting compounds of formula (I) and formula (II) can be reacted efficiently and the unreacted compound of formula (I) in the reaction solvent can be reduced. In particular, in case where the starting compound of formula (I) has good crystallinity, then the unnecessary compound of formula (I) may mix in the intended product compound of formula (III) when the product of formula (III) is isolated and purified through crystallization or recrystallization, and therefore the isolation and purification of the product may be insufficient. Accordingly, it is desirable that the amount of the unreacted compound of formula (I) to be in the reaction solvent is small.

Not specifically defined, the carbonate includes, for example, salts of carbonic acid with an alkali metal, such as sodium carbonate, potassium carbonate, sodium potassium carbonate; salts of carbonic acid with an alkaline earth metal, such as magnesium carbonate, calcium carbonate; and hydrogencarbonates such as sodium hydrogencarbonate, potassium hydrogencarbonate. Of those, a preferred example is potassium carbonate. Preferably, the carbonate to be used herein is finely ground. The reason is because, it has been found that, if a large amount of the starting compound of formula (I) remains in a crystal of the product, the intended compound of formula (III), then the compound is extremely difficult to remove from the product in the purification operation such as salt formation of recrystallization, and it has also been found that the residual percentage of the unreacted compound of formula (I) increases depending on the difference in the particle size of the carbonate (Examples 4 and 5).

The carbonate may be ground in any ordinary method with a jet mill, a pin mill, a hammer mill or the like. In the invention, however, the carbonate ground with a jet mill may have a favorable particle size. Simultaneously with stirring it, the carbonate may be ground with a stirrer. However, in an industrial process, the reaction is generally attained with a stirring blade, and the carbonate could not be expected to be ground with the stirring blade during reaction. Accordingly, a preliminary ground carbonate is preferably used herein.

Not specifically defined, the mean particle size of the ground carbonate for use in the invention is preferably such that, in HPLC analysis of the reaction solution after reaction, the relative area percentage of the peak derived from the compound of formula (I) could be at most about 1.0%, more preferably, at most 1.0%. On the other hand, not also specifically defined, the lowermost limit is preferably at least 0%. From this viewpoint, the mean particle size of the ground particle size is preferably at most about 10 micrometers, more preferably at most 10 micrometers (see Example 5). On the other hand, not also specifically defined, the lowermost limit is preferably at least 1 micrometer. This is because some carbonates such as potassium carbonate are deliquescent, and if too much ground, they may readily absorb water.

The reaction solvent may be any ordinary solvent for organic compounds, not including water so as not promote hydrolysis of the ester in the workup step, but capable of giving the compound of formula (III). Its examples are, for example, alcohols such as methanol, ethanol; hydrocarbons such as hexane, benzene; carbonyl group-having solvents such as acetone, methyl ethyl ketone. Preferred is a carbonyl group-having solvent; and more preferred is methyl ethyl ketone.

Apart from a free form thereof, the compound of formula (I) may be in any form of salt, hydrate or solvate. Not specifically defined at all, the morphology of the compound is preferably a crystal from the viewpoint of the easiness in isolation and purification thereof and of the possibility of accurate measurement thereof. Of the compounds of formula (I), those having good crystallinity are solvates of (1R)-1-(3-chlorophenyl)-2-[(1R,3R)-3-(3-hydroxyphenyl)cyclohexylamino]ethanol, concretely including (1R)-1-(3-chlorophenyl)-2-[(1R,3R)-3-(3-hydroxyphenyl)cyclohexylamino]ethanol 1/3 toluene-solvate and (1R)-1-(3-chlorophenyl)-2-[(1R,3R)-3-(3-hydroxyphenyl)cyclohexylamino]ethanol 1/3 ethyl acetate-solvate.

Examples of pharmaceutically-acceptable salts of the compound of formula (III) include, for example, salts with inorganic acids such as hydrochloric acid, nitric acid, sulfuric acid, hydrobromic acid, hydroiodic acid, phosphoric acid; and salts with organic salts such as acetic acid, tartaric acid, fumaric acid, maleic acid, malic acid, methanesulfonic acid, ethanesulfonic acid, camphorsulfonic acid, benzenesulfonic acid, toluenesulfonic acid, to which, however, the invention should not be limited. Of those salts, preferred are salts with organic acids; and more preferred are salts with maleic acid.

EXAMPLES

The invention is described more concretely with reference to the following Examples, which, however, are not intended to restrict the scope of the invention to the following Examples.

Example 1

Production of (1R)-1-(3-chlorophenyl)-2-[(1R,3R)-3-(3-hydroxyphenyl)cyclohexylamino]ethanol 1/3 toluene-solvate crystal A mixture of 10 ml of toluene, 1.92 g of (1R,3R)-3-(3-hydroxyphenyl)cyclohexylamine and 1.55 g of (R)-3-chlorostyrene oxide was heated under reflux for 4 hours. The reaction liquid was cooled to room temperature, a seed crystal was inoculated into it, and stirred as such for 30 minutes. The precipitated crystal was taken out through filtration, and then dried under aeration at 50° C. for 2.5 hours to obtain 2.42 g of the entitled compound.

$^1$H—NMR (CDCl$_3$) δ: 1.40-1.89 (8H, m), 2.36 (1H, s), 2.65-3.06 (4H, m), 4.72-4.77 (1H, m), 6.64-6.77 (3H, m), 7.12-7.26 (5.67H, m), 7.37 (1H, m).

Preparation of Sample for Elementary Analysis:

4.0 g of crude (1R)-1-(3-chlorophenyl)-2-[(1R,3R)-3-(3-hydroxyphenyl)cyclohexylamino]ethanol 1/3 toluene-solvate was purified through column chromatography, 15 ml of toluene was added to the resulting oily matter and heated. After cooled, the precipitated crystal was taken out through filtration, dried through aeration at 50° C., and then dried under reduced pressure at 60° C. to obtain 1.39 g of the intended compound.

Elementary Analysis, as $C_{20}H_{24}ClNO_2$ 1/3$C_7H_8$:

| Found: | C 71.28%; H 7.20%; N 3.48% |
|---|---|
| Calculated | C 71.23%; H 7.14%; N 3.72% |

Example 2

Production of ethyl 3-[(1R,3R)-3-[(2R)-2-(3-chlorophenyl)-2-hydroxyethylamino]cyclohexyl]phenoxy acetate maleate A mixture of 60 g of (1R)-1-(3-chlorophenyl)-2-[(1R,3R)-3-(3-hydroxyphenyl)cyclohexylamino]ethanol 1/3 toluene-solvate, 450 ml of methyl ethyl ketone, and 66.1 g of potassium carbonate ground with a jet mill was heated under reflux for 1 hour. With heating, a methyl ethyl ketone (30 ml) solution of 31.9 g of ethyl bromoacetate was dropwise added to the mixture liquid, and then further heated under reflux for 5 hours. After cooled, this was filtered through Celite, and a methyl ethyl ketone (270 ml) solution of 18.9 g of maleic acid was put into the resulting solution, and stirred for 1 hour with cooling with ice. The precipitated crystal was taken out through filtration, and the crystal was washed with methyl ethyl ketone and dried under reduced pressure to obtain 63.2 g of a crude crystal of the entitled compound.

The obtained crude crystal was recrystallized from ethanol to obtain 56.3 g of the entitled compound.

$^1$H—NMR (DMSO-$d_6$) δ: 1.19 (3H, t, J=7.02 Hz), 1.51-2.04 (8H, m), 2.98-3.43 (4H, m), 4.15 (2H, q, J=7.02 Hz), 4.74 (2H, s), 4.93-4.96 (1H, m), 6.03 (2H, s), 6.73-6.91 (3H, m), 7.20-7.49 (5H, m)

Example 3

Production of (1R)-1-(3-chlorophenyl)-2-[(1R,3R)-3-(3-hydroxyphenyl)cyclohexylamino]ethanol 1/3 ethyl acetate-solvate crystal 0.50 g of (1R)-1-(3-chlorophenyl)-2-[(1R,3R)-3-(3-hydroxyphenyl)cyclohexylamino]ethanol 1/3 toluene-solvate was dissolved in 10 ml of ethyl acetate, and the solvent was evaporated away under reduced pressure. The same operation was repeated twice, and the obtained crystal was dried under reduced pressure to obtain 0.37 g of the entitled compound.

3-[(1R,3R)-3-[(2R)-2-(3-chlorophenyl)-2-hydroxyethylamino]cyclohexyl]phenoxyacetate (intended product). In the relative area percentage method as employed herein, the proportion of the intended peak area to the sum total of the detected peak area is expressed as percentage. In this, the peak for maleic acid was excluded for the computation.

Reaction Example

A methyl ethyl ketone mixture liquid of 1 equivalent of (1R)-1-(3-chlorophenyl)-2-[(1R,3R)-3-(3-hydroxyphenyl)cyclohexylamino]ethanol 1/3 toluene-solvate and from 2.0 to 3.0 equivalents of potassium carbonate was heated under reflux. With heating, a methyl ethyl ketone solution of from 1.0 to 1.2 equivalents of ethyl bromoacetate was dropwise added to the mixture liquid, and further heated under reflux for 3 to 4 hours. A part of the reaction liquid was sampled, and subjected to HPLC analysis. After cooled, this was filtered through Celite, and a methyl ethyl ketone solution of 1.0 equivalent of maleic acid was put into the obtained solution, and stirred. The precipitated crystal was taken out through filtration, and dried through aeration to obtain ethyl 3-[(1R,3R)-3-[(2R)-2-(3-chlorophenyl)-2-hydroxyethylamino]cyclohexyl]phenoxyacetate maleate. The obtained crystal was subjected to HPLC analysis, in which the content of (1R)-1-(3-chlorophenyl)-2-[(1R,3R)-3-(3-hydroxyphenyl)cyclohexylamino]ethanol (starting compound) and the content of ethyl 3-[(1R,3R)-3-[(2R)-2-(3-chlorophenyl)-2-hydroxyethylamino]cyclohexyl]phenoxyacetate (target product) in the crystal were determined according to the above-mentioned relative area percentage method.

| | | Potassium Carbonate | | | | HPLC Relative Area Percentage | | | |
| | | | | | | in reaction solution | | obtained crystal | |
| Entry | Source | Equivalent Number (equivalent) | Ethyl Bromoacetate (equivalent) | Reaction Time (hour) | Yield of Product (%) | starting compound (%) | product (%) | starting compound (%) | product (%) |
|---|---|---|---|---|---|---|---|---|---|
| 1 | untreated | 3.0 | 1.2 | 3 | 49.1 | 13.8 | 70.57 | 11.26 | 87.98 |
| 2 | ground in mortar | 2.0 | 1.0 | 7 | 77.7 | ND | ND | 6.8 | 95.9 |

ND: This means no data obtained.
"ground in mortar" means that the carbonate was ground with an agate mortar for 5 minutes and used.

$^1$H—NMR (CDCl$_3$) δ: 1.26 (1H, t, J=7.20 Hz), 1.40-1.90 (8H, m), 2.05 (1H, s), 2.65-3.06 (4H, m), 4.12 (0.67H, q, J=7.20 Hz), 4.72-4.75 (1H, m), 6.65-6.78 (3H, m), 7.12-7.26 (4H, m), 7.38 (1H, s)

Example 4

Investigation of Influence of Carbonate Grinding Method on Reaction

The reaction liquids and the crystals obtained according to the production method mentioned below, using two types of potassium carbonate that differ in their processing method (one is a commercially-available product potassium carbonate (by Wako Pure Chemical Industries), and this was used directly as it was; and the other was ground with an agate mortar before use), was analyzed through HPLC (relative area percentage method) for the content of (1R)-1-(3-chlorophenyl)-2-[(1R,3R)-3-(3-hydroxyphenyl)cyclohexylamino]ethanol (starting compound) and the content of ethyl (HPLC Condition)
  HPLC: Shimadzu's CLASS-VP Series
  Column: CAPCELLPAK UG-120 (4.6×φ150 mm) (by Shiseido)
  Solvent: acetonitrile/aqueous solution of 50 mM ammonium dihydrogenphosphate=40/60
  Flow rate: 1.0 ml/min
  Column temperature: 35° C.
  Detection wavelength: 220 nm

Example 5

Investigation of Fine Powder Carbonate for Use in Reaction

The crystals obtained according to the production method mentioned below, using three types of fine powdery potassium carbonate bought in a market, and one type of potassium carbonate ground with a jet mill, were analyzed through HPLC (relative area percentage method) for the content of (1R)-1-(3-chlorophenyl)-2-[(1R,3R)-3-(3-hydroxyphenyl) cyclohexylamino]ethanol (starting compound) and the content of ethyl 3-[(1R,3R)-3-[(2R)-2-(3-chlorophenyl)-2-hydroxyethylamino]cyclohexyl]phenoxyacetate (target product).

Reaction Example

A methyl ethyl ketone mixture liquid of 1 equivalent of (1R)-1-(3-chlorophenyl)-2-[(1R,3R)-3-(3-hydroxyphenyl) cyclohexylamino]ethanol 1/3 toluene-solvate and from 3.0 equivalents of potassium carbonate was heated under reflux for 2 hours. With heating, a methyl ethyl ketone solution of 1.2 equivalents of ethyl bromoacetate was dropwise added to the mixture liquid, and further heated under reflux for 3 hours. A part of the reaction liquid was sampled, and subjected to HPLC analysis. After cooled, this was filtered through Celite, and a methyl ethyl ketone solution of 1.0 equivalent of maleic acid was put into the obtained solution, and stirred at room temperature for 30 minutes, and then, with cooling with ice, for 30 minutes. The precipitated crystal was taken out through filtration, then washed with methyl ethyl ketone, and dried through aeration to obtain ethyl 3-[(1R,3R)-3-[(2R)-2-(3-chlorophenyl)-2-hydroxyethylamino]cyclohexyl]phenoxyacetate maleate. The obtained crystal was subjected to HPLC analysis, in which the content of (1R)-1-(3-chlorophenyl)-2-[(1R,3R)-3-(3-hydroxyphenyl)cyclohexylamino]ethanol (starting compound) and the content of ethyl 3-[(1R,3R)-3-[(2R)-2-(3-chlorophenyl)-2-hydroxyethylamino]cyclohexyl]phenoxyacetate (target product) in the crystal were determined according to the above-mentioned relative area percentage method.

| | | Potassium Carbonate Mean Particle Size (μm) | Amount of Product (g) | Yield of Product (%) | HPLC Relative Area Percentage | | | |
|---|---|---|---|---|---|---|---|---|
| | | | | | in reaction solution | | obtained crystal | |
| Entry | Supplier | | | | starting compound (%) | product (%) | starting compound (%) | product (%) |
| 1 | Asahi Glass | 18.9 | 5.16 | 59.1 | 9.90 | 84.10 | 7.30 | 92.00 |
| 2 | Nippon Soda | 12.7 | 5.92 | 67.8 | 3.79 | 83.04 | 3.02 | 95.69 |
| 3 | Nippon Soda | 13.2 | 5.86 | 67.1 | 4.74 | 91.64 | 3.74 | 95.57 |
| 4 | jet-mill ground powder | 8.96 | 6.53 | 74.8 | 0.04 | 93.15 | — | 99.02 |
| 5 | jet-mill ground powder | 9.76 | 5.41 | 74.2 | 0.85 | 90.25 | 0.09 | 99.11 |

(Note)
In Entry 5, the amount of the starting compound used was 5.0 g; and in the others, it was 6.0 g.

(Note)
Commercial products of potassium carbonate by Nippon Soda and Asahi Glass are both fine powdery, and they were used directly as they were. The jet-mill ground powders were prepared from a commercially-available granular potassium carbonate (by Kokusan Chemical Co.) by grinding it with a jet mill (Seishin Enterprise's jet mill grinding machine, CP-10 Model), under the condition mentioned below.

(Grinding Condition)

Under a pneumatic pressure of from 5 to 6 kg/cm², potassium carbonate was put into a vertical track mill at a rate of from 15 to 20 g/min, and ground therein.

(HPLC Condition)

HPLC: Shimadzu's CLASS-VP Series

Column: CAPCELLPAK UG-120 (4.6×φ150 mm) (by Shiseido)

Solvent: acetonitrile/aqueous solution of 50 mM ammonium dihydrogenphosphate=40/60

Flow rate: 1.0 ml/min

Column temperature: 35° C.

Detection wavelength: 220 nm (Method for Measurement of Mean Particle Size)

10 to 15 mg of potassium carbonate was added to 40 ml of n-BuOH, and after 1 minute, this was measured while irradiated with ultrasonic waves.

Device used for Measurement: Shimadzu Laser Refractory Particle Sizer, SADL-1100 Model

INDUSTRIAL APPLICABILITY

According to the invention, a compound of the following general formula (I):

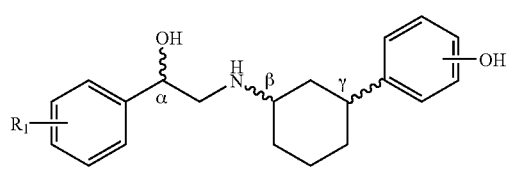

(I)

(wherein $R_1$ represents a hydrogen atom or a halogen atom) may be directly and highly selectively alkylated (this includes alkoxycarbonylalkylation) at its phenolic hydroxyl group, thereby efficiently producing a compound of the following formula (III):

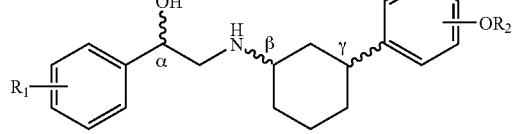

(III)

(wherein $R_1$ represents a hydrogen atom or a halogen atom; R2 represents an alkyl group optionally substituted with an alkoxycarbonyl group). In addition, the invention provides an intermediate with good crystallinity, suitable to the production of the compound of formula (III).

The present application is based on Japanese Patent Application No. 2004-305296 filed in Japan, the entire contents thereof being hereby incorporated in this description.

The invention claimed is:

1. A production method of a compound represented by the following general formula (III) or its pharmaceutically-acceptable salt, or their hydrate or solvate:

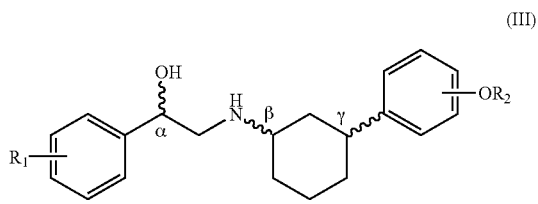

(III)

(wherein $R_1$ represents a hydrogen atom or a halogen atom; $R_2$ represents an alkyl group optionally substituted with an alkoxycarbonyl group), which comprises reacting, without protecting the amino group thereof, a compound represented by the following general formula (I):

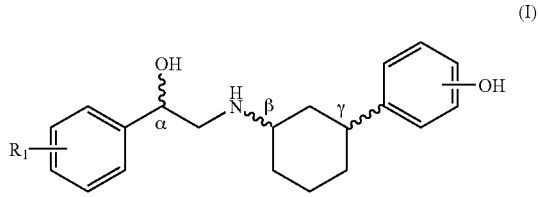

(I)

(wherein $R_1$ represents a hydrogen atom or a halogen atom), with a compound represented by the following general formula (II):

$R_2$—X   (II)

(wherein $R_2$ represents an alkyl group optionally substituted with an alkoxycarbonyl group; X represents a halogen atom) in the presence of a carbonate.

2. The production method as claimed in claim 1, wherein the compound represented by formula (I) is obtained by reacting a compound represented by the following general formula (IV):

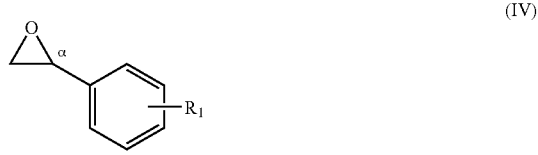

(IV)

(wherein $R_1$ represents a hydrogen atom or a halogen atom), with a compound represented by the following formula (V):

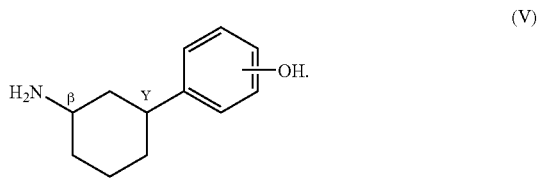

(V)

3. The production method as claimed in claim 1, wherein the compound represented by formula (I) or its solvate is reacted with the compound represented by formula (II) in the presence of potassium carbonate.

4. The production method as claimed in claim 1, wherein the compound represented by formula (I) or its solvate is reacted with the compound represented by formula (II) in the presence of finely-ground potassium carbonate.

5. The production method as claimed in claim 1, wherein the compound represented by formula (I) or its solvate is reacted with the compound represented by formula (II) in a carbonyl group-having solvent.

6. The production method as claimed in claim 1, wherein the compound represented by formula (I) is reacted with the compound represented by formula (II) in methyl ethyl ketone.

7. The production method as claimed in claim 1, wherein $R_1$ is a halogen atom.

8. The production method as claimed in claim 1, wherein $R_1$ is a chlorine atom.

9. The production method as claimed in claim 1, wherein $R_2$ is a methyl group substituted with one alkoxycarbonyl group having from 2 to 5 carbon atoms.

10. The production method as claimed in claim 1, wherein $R_2$ is an ethoxycarbonylmethyl group.

11. The production method as claimed in claim 1, wherein the absolute configuration of the asymmetric carbon α is R-configuration.

12. The production method as claimed in claim 1, wherein the absolute configuration of the asymmetric carbon β is R-configuration.

13. The production method as claimed in claim 1, wherein the absolute configuration of the asymmetric carbon γ is R-configuration.

14. The production method as claimed in claim 1, wherein the compound represented by formula (I) or its solvate is a solvate of (1R)-1-(3-chlorophenyl)-2-[(1R,3R)-3-(3-hydroxyphenyl)cyclohexylamino]ethanol.

15. The production method as claimed in claim 1, wherein the compound represented by formula (I) or its solvate is (1R)-1-(3-chlorophenyl)-2-[(1R,3R)-3-(3-hydroxyphenyl)cyclohexylamino]ethanol 1/3 toluene-solvate.

16. The production method as claimed in claim 1, wherein the compound represented by formula (I) or its solvate is (1R)-1-(3-chlorophenyl)-2-[(1R,3R)-3-(3-hydroxyphenyl)cyclohexylamino]ethanol 1/3 ethyl acetate-solvate.

17. The production method as claimed in claim 1, wherein the compound represented by formula (I) or its solvate is a crystal of a solvate of (1R)-1-(3-chlorophenyl)-2-[(1R,3R)-3-(3-hydroxyphenyl)cyclohexylamino]ethanol.

18. The production method as claimed in claim 1, wherein the compound represented by formula (I) or its solvate is a crystal of (1R)-1-(3-chlorophenyl)-2-[(1R,3R)-3-(3-hydroxyphenyl)cyclohexylamino]ethanol 1/3 toluene-solvate.

19. The production method as claimed in claim 1, wherein the compound represented by formula (I) or its solvate is a crystal of (1R)-1-(3-chlorophenyl)-2-[(1R,3R)-3-(3-hydroxyphenyl)cyclohexylamino]ethanol 1/3 ethyl acetate-solvate.

20. The production method as claimed in claim 1, wherein the pharmaceutically-acceptable salt of the compound represented by formula (III) is a maleate.

21. The production method as claimed in claim 1, which comprises reacting a crystal of (1R)-1-(3-chlorophenyl)-2-[(1R,3R)-3-(3-hydroxyphenyl)cyclohexylamino]ethanol 1/3 toluene-solvate as a starting material, with ethyl bromoacetate in methyl ethyl ketone in the presence of potassium carbonate, and adding maleic acid thereto.

22. The production method as claimed in claim 1, which comprises reacting a crystal of (1R)-1-(3-chlorophenyl)-2-[(1R,3R)-3-(3-hydroxyphenyl)cyclohexylamino]ethanol 1/3 toluene-solvate as a starting material, with ethyl bromoacetate in methyl ethyl ketone in the presence of finely-ground potassium carbonate, and adding maleic acid thereto.

23. The production method as claimed in claim 1, which comprises reacting a crystal of (1R)-1-(3-chlorophenyl)-2-[(1R,3R)-3-(3-hydroxyphenyl)cyclohexylamino]ethanol 1/3 ethyl acetate-solvate as a starting material, with ethyl bromoacetate in methyl ethyl ketone in the presence of potassium carbonate, and adding maleic acid thereto.

24. The production method as claimed in claim 1, which comprises reacting a crystal of (1R)-1-(3-chlorophenyl)-2-[(1R,3R)-3-(3-hydroxyphenyl)cyclohexylamino]ethanol 1/3 ethyl acetate-solvate as a starting material, with ethyl bromoacetate in methyl ethyl ketone in the presence of fine-ground potassium carbonate, and adding maleic acid thereto.

25. The production method as claimed in claim 1, wherein in HPLC analysis of the reaction solution after the reaction, the relative area percentage of the peak derived from the compound represented by formula (I) or its solvate, (1R)-1-(3-chlorophenyl)-2-[(1R,3R)-3-(3-hydroxyphenyl)cyclohexylamino]ethanol 1/3 toluene-solvate, or (1R)-1-(3-chlorophenyl)-2-[(1R,3R)-3-(3-hydroxyphenyl)cyclohexylamino]ethanol 1/3-ethyl acetate solvate is at most about 1.0 %.

26. The production method as claimed in claim 1, wherein the carbonate is ground with a jet mill.

27. The production method as claimed in claim 26, wherein the carbonate has a mean particle size of at most about 10 micrometers.

* * * * *